US009233368B2

(12) United States Patent
Bau et al.

(10) Patent No.: US 9,233,368 B2
(45) Date of Patent: Jan. 12, 2016

(54) MOISTURE-ACTIVATED SELF-HEATING ANALYSIS DEVICE

(75) Inventors: Haim H. Bau, Swarthmore, PA (US); Changchun Liu, Philadelphia, PA (US); Michael G. Mauk, Wilmington, DE (US); Robert W. Hart, Philadelphia, PA (US); Xianbo Qiu, Philadelphia, PA (US)

(73) Assignee: The Trustees Of The University Of Pennsylvania, Philadelphia, PA (US)

( * ) Notice: Subject to any disclaimer, the term of this patent is extended or adjusted under 35 U.S.C. 154(b) by 373 days.

(21) Appl. No.: 13/477,332

(22) Filed: May 22, 2012

(65) Prior Publication Data

US 2012/0315638 A1 Dec. 13, 2012

Related U.S. Application Data

(60) Provisional application No. 61/488,823, filed on May 23, 2011.

(51) Int. Cl.
*C12Q 1/68* (2006.01)
*B01L 3/00* (2006.01)
*B01L 7/00* (2006.01)

(52) U.S. Cl.
CPC ............... *B01L 3/5027* (2013.01); *B01L 7/525* (2013.01); *C12Q 1/6806* (2013.01); *B01L 3/502707* (2013.01); *B01L 2200/148* (2013.01); *B01L 2300/0681* (2013.01); *B01L 2400/0406* (2013.01); *B01L 2400/0481* (2013.01)

(58) Field of Classification Search
CPC .................. B01L 2200/148; B01L 2300/0681; B01L 2400/0406; B01L 2400/0481; B01L 3/5027; B01L 3/502707; B01L 7/525; C12Q 1/6806
USPC ........................................................ 435/91.2
See application file for complete search history.

(56) References Cited

U.S. PATENT DOCUMENTS

| | | |
|---|---|---|
| 4,106,477 A | 8/1978 | Feld |
| 5,611,329 A | 3/1997 | Lamensdorf |
| 5,984,953 A | 11/1999 | Sabin et al. |
| 6,231,596 B1 | 5/2001 | Collins |
| 6,537,309 B2 | 3/2003 | Sharma et al. |

FOREIGN PATENT DOCUMENTS

WO WO 2011014449 * 2/2011

OTHER PUBLICATIONS

U.S. Appl. No. 61/446,850, filed Feb. 25, 2011, Bau.
Asiello et al., "Miniaturized isothermal nucleic acid amplification, a review", Lab Chip, Mar. 2011, 11(8), 1420-1430.
Bonacorsi et al., "Molecular epidemiology of *Escherichia coli* causing neonatal meningitis", Int. J. Med. Microbiol., Oct. 2005, 295(6-7), 373-381.
Chen et al., "A Microfluidic System for Saliva-Based Detection of Infectious Diseases", Ann. N. Y. Acad. Sci., Mar. 2007, 1098, 429-436.
Chen et al., "An integrated, self-contained microfluidic cassette for isolation, amplification, and detection of nucleic acids", Biomed. Microdevices, Aug. 2010, 12(4), 705-719.
Chen et al., "Continuous flow microfluidic device for cell separation, cell lysis and DNA purification", Anal. Chim. Acta, Feb. 2007, 584(2), 237-243.
Cheng et al., "Enhancing the performance of a point-of-care CD4+ T-cell counting microchip through monocyte depletion for HIV/AIDS diagnostics", Lab Chip, May 2009, 9(10), 1357-1364.
Clarke, "Diarrhoeagenic *Escherichia coli*—an emerging problem?", Diagn. Microbiol. Infect. Dis., Nov. 2001, 41(3), 93-98.
Compton, "Nucleic acid sequence-based amplification", Nature, Mar. 1991, 350, 91-92.
Curtis et al., "Rapid detection of HIV-1 by reverse-transcription, loop-mediated isothermal amplification (RT-LAMP)", J. Virol. Meth., Aug. 2008, 151(2), 264-270.
Dineva et al., "Sample preparation: a challenge in the development of point-of-care nucleic acid-based assays for resource-limited settings", Analyst, Oct. 2007, 132(12), 1193-1199.
Fang et al., "Loop-Mediated Isothermal Amplification Integrated on Microfluidic Chips for Point-of-Care Quantitative Detection of Pathogens", Anal. Chem., Mar. 2010, 82(7), 3002-3006.
Gibellini et al., "Quantitative detection of human immunodeficiency virus type 1 (HIV-1) viral load by SYBR green real-time RT-PCR technique in HIV-1 seropositive patients", J. Virol. Methods, Feb. 2004, 115(2), 183-189.
Gulliksen et al., "Parallel nanoliter detection of cancer markers using polymer microchips", Lab Chip, Apr. 2005, 5(4), 416-420.
Hatano et al., "LAMP using a disposable pocket warmer for anthrax detection, a highly mobile and reliable method for anti-bioterrorism", J. Infect. Dis., Jan. 2010, 63(1), 36-40.
Hill et al., "Loop-Mediated Isothermal Amplification Assay for Rapid Detection of Common Strains of *Escherichia coli*", J. Clin. Microbiol., Aug. 2008, 46(8), 2800-2804.
Johnson, J. R., "Microbial virulence determinants and the pathogenesis of urinary tract infection," Infect. Dis. Clin. North Am., Jun. 2003, 17(2), 261-278.
Jokerst et al., "Integration of semiconductor quantum dots into nano-bio-chip systems for enumeration of CD4+ T cell counts at the point-of-need", Lab Chip, Dec. 2008, 8(12), 2079-2090.
Kim et al., "A disposable, self-contained PCR chip," Lab Chip, Feb. 2009, 9(4), 606-612.
Klein et al., "Diarrhea Etiology in a Children's Hospital Emergency Department: A Prospective Cohort Study", Clin. Infect. Dis., Oct. 2006, 43(7), 807-813.

(Continued)

*Primary Examiner* — Cynthia B Wilder
(74) *Attorney, Agent, or Firm* — Baker & Hostetler LLP

(57) ABSTRACT

Provided are disposable, moisture-activated, self-heating cartridges useful for, e.g., isothermal nucleic acid amplification, incubation, and thermal actuation, and visual fluorescent detection of the amplification products. These devices may be self-contained and do not require any special instruments to operate.

10 Claims, 11 Drawing Sheets

(56) References Cited

OTHER PUBLICATIONS

LaBarre et al., "Non-instrumented nucleic acid amplification (NINA): Instrument-free molecular malaria diagnostics for low-resource settings", IEEE Eng. Med. Biol. Soc., Aug. 31-Sep. 4, 2010, 1097-1099.

Lee et al., "A polymer lab-on-a-chip for reverse transcription (RT)-PCR based point-of-care clinical diagnostics", Lab Chip, Oct. 2008, 8(12), 2121-2127.

Liu et al., "A disposable integrated loop-mediated isothermal amplification cassette with thermally actuated valves", Microfluidics and Nanofluidics, Aug. 2011, 11(2), 209-220.

Liu et al., "A membrane-based, high-efficiency, microfluidic debubbler", Lab Chip, Mar. 2011, 11(9), 1688-1693.

Liu et al., "A self-heating cartridge for molecular diagnostics", Lab Chip, Jul. 2011, 11(16), 2686-2692.

Liu et al., "A timer-actuated immunoassay cassette for detecting molecular markers in oral fluids", Lab Chip, Mar. 2009, 9(6), 768-776.

Liu et al., "An isothermal amplification reactor with an integrated isolation membrane for point-of-care detection of infectious diseases", Analyst, May 2011, 136(10), 2069-2076.

Liu et al., "Integrated DNA purification, PCR, sample cleanup, and capillary electrophoresis microchip for forensic human identification", Lab Chip, Feb. 2011, 11(6), 1041-1048.

Liu, "Rapid fabrication of microfluidic chip with three-dimensional structures using natural lotus leaf template", Microfluid. Nanofluid., Apr. 2010, 9(4-5), 923-931.

Lutz et al., "Microfluidic lab-on-a-foil for nucleic acid analysis based on isothermal recombinase polymerase amplification (RPA)," Lab Chip, Jan. 2010, 10(7), 887-893.

Marrs et al., "*Escherichia coli* mediated urinary tract infections: Are there distinct uropathogenic *E. coli* (UPEC) pathotypes?", FEMS Microbiol. Lett., Sep. 2005, 252, 183-190.

Mehta et al., "Low-Cost HIV-1 Diagnosis and Quantification in Dried Blood Spots by Real Time PCR", PLoS One, Jun. 2009, 4(6), e5819, 1-10.

Mori et al., "Detection of Loop-Mediated Isothermal Amplification Reaction by Turbidity Derived from Magnesium Pyrophosphate Formation", Biochem. Biophys. Res. Commun., Nov. 2001, 289(1), 150-154.

Murray et al., "Update on Rapid Diagnostic Testing for Malaria", Clin. Microbiol. Rev., Jan. 2008, 21(1), 97-110.

Notomi et al., "Loop-mediated isothermal amplification of DNA", Nucleic Acids Res., Jun. 2000, 28(12), e63, 1-7.

Piepenburg et al., "DNA Detection Using Recombination Proteins", PLoS Biol., Jul. 2006, 4(7), e204, 1115-1121.

Qiu et al., "Finger-actuated, self-contained immunoassay cassettes", Biomed. Microdevices, Dec. 2009, 11(6), 1175-1186.

Ramalingam et al., "Microfluidic devices harboring unsealed reactors for real-time isothermal helicase-dependent amplification", Microfluid. Nanofluid., Sep. 2009, 7(3), 325-336.

Rouet et al., "Transfer and Evaluation of an Automated, Low-Cost Real-Time Reverse Transcription-PCR Test for Diagnosis and Monitoring of Human Immunodeficiency Virus Type 1 Infection in a West African Resource-Limited Setting", J. Clin. Microbiol., Jun. 2005, 43(6), 2709-2717.

Sato et al., "Microbead-based rolling circle amplification in a microchip for sensitive DNA detection", Lab Chip, May 2010, 10(10), 1262-1266.

Walker et al., "Strand displacement amplification—an isothermal, in vitro DNA amplification technique", Nucleic Acids Res., Apr. 1992, 20(7), 1691-1696.

Wang et al., "A disposable microfluidic cassette for DNA amplification and detection," Lab Chip, Jan. 2006, 6(1), 46-53.

Weigl et al., "Non-instrumented Nucleic-Acid Amplification Assay", Proc. SPIE, Mar. 2008, 6886, 688604-1-688604-12.

Weigl et al., "Towards non- and minimally instrumented, microfluidics-based diagnostic devices", Lab Chip, Dec. 2008, 8(12), 1999-2014.

Wong, R., "The effect of adulterants on urine screen for drugs of abuse: detection by an on-site dipstick device," Am. Clin. Lab., Jan.-Feb. 2002, 21(1), 37-39.

Yager et al., "Microfluidic diagnostic technologies for global public health", Nature, Jul. 2006, 442, 412-418.

Zhang et al., "Miniaturized PCR chips for nucleic acid amplification and analysis: latest advances and future trends", Nucleic Acids Res., Jul. 2007, 35(13), 4223-4237.

\* cited by examiner

MOISTURE-ACTIVATED SELF-HEATING ANALYSIS DEVICE

RELATED APPLICATION

The present application claims priority to U.S. Patent Application No. 61/488,823, "Moisture-Activated Self-Heating Analysis Devices," filed May 23, 2011, and incorporated herein by reference in its entirety for any and all purposes.

SEQUENCE LISTING

The instant application contains a Sequence Listing which has been submitted electronically in ASCII format and is hereby incorporated by reference in its entirety. Said ASCII copy, created on Nov. 4, 2014, is named 103241.005752-X5912_SL.txt and is 1,716 bytes in size.

GOVERNMENT RIGHTS

This invention was supported by NIH/NIDCR grant U01DE017855. The government has certain rights in this invention.

TECHNICAL FIELD

The present disclosure relates to the field of microfluidic devices.

BACKGROUND

In recent years, there has been a growing interest in inexpensive, point of care diagnostics for home care, individualized medicine, and therapeutics. Such devices also address medical needs in regions of the world lacking sophisticated laboratory facilities. Because many chemical and biological reactions of interest (e.g., enzymatic amplification reactions) require elevated temperature, there is a need in the art for portable microfluidic devices having the capability of supplying thermal energy to reactants.

SUMMARY

In one embodiment, the present disclosure presents devices, comprising a heating material that undergoes an exothermic reaction upon contact with a fluid; a thermal storage medium in thermal communication with the heat source, the thermal storage medium comprising a phase-changing material; a conduit placing the heating material in fluid communication with a reservoir adapted to contain a fluid, and the conduit comprising a material capable of transporting liquid by capillary action.

The present disclosure also presents methods of processing a sample, comprising contacting a moisture-reactive heat source with a fluid so as to generate heat; the moisture-reactive heat source being in thermal communication with a thermal storage medium (which may also be referred to as a heat sink, in some cases), the moisture-reactive heat source and thermal storage medium being configured to maintain the temperature of a sample in a reaction vessel adjacent to the water-sensitive heat source. The source can also be used to actuate (e.g., shrink or open) pouches to displace fluids and can also be used to open or close valves.

The general description and the following detailed description are exemplary and explanatory only and are not restrictive of the invention, as defined in the appended claims. Other aspects of the present invention will be apparent to those skilled in the art in view of the detailed description of the invention as provided herein.

BRIEF DESCRIPTION OF THE DRAWINGS

The summary, as well as the following detailed description, is further understood when read in conjunction with the appended drawings. For the purpose of illustrating the invention, there are shown in the drawings exemplary embodiments of the invention; however, the invention is not limited to the specific methods, compositions, and devices disclosed. In addition, the drawings are not necessarily drawn to scale. In the drawings.

DETAILED DESCRIPTION OF ILLUSTRATIVE EMBODIMENTS

Figure 1:
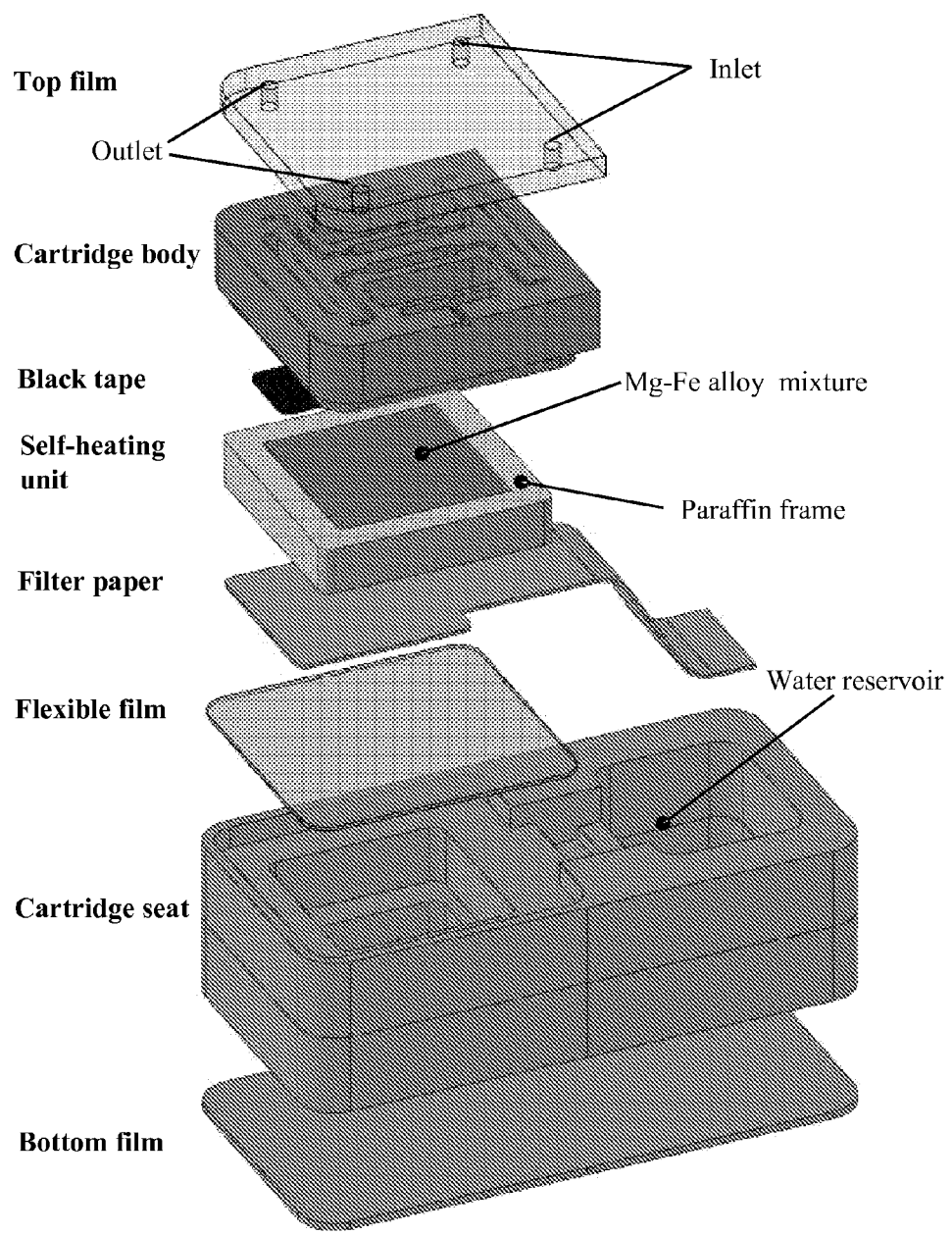
FIG. 1: Exploded view of an exemplary water-actuated, self-heating, non-instrumented cartridge for isothermal amplification of nucleic acids. The cartridge consists of two main components: a cartridge body and a cartridge seat.

The present invention may be understood more readily by reference to the following detailed description taken in connection with the accompanying figures and examples, which form a part of this disclosure. It is to be understood that this invention is not limited to the specific devices, methods, applications, conditions or parameters described and/or shown herein, and that the terminology used herein is for the purpose of describing particular embodiments by way of example only and is not intended to be limiting of the claimed invention. Also, as used in the specification including the appended claims, the singular forms "a," "an," and "the" include the plural, and reference to a particular numerical value includes at least that particular value, unless the context clearly dictates otherwise. The term "plurality", as used herein, means more than one. When a range of values is expressed, another embodiment includes from the one particular value and/or to the other particular value. Similarly, when values are expressed as approximations, by use of the antecedent "about," it will be understood that the particular value forms another embodiment. All ranges are inclusive and combinable.

It is to be appreciated that certain features of the invention which are, for clarity, described herein in the context of separate embodiments, may also be provided in combination in a single embodiment. Conversely, various features of the invention that are, for brevity, described in the context of a single embodiment, may also be provided separately or in any subcombination. Further, reference to values stated in ranges include each and every value within that range. All documents mentioned herein are incorporated by reference in their entireties for any and all purposes.

In one exemplary embodiment, the present disclosure provides water-activated, self-heating, microfluidic cartridge for isothermal nucleic acid amplification. The device does not require any external instrument and/or power. The device is powered by an exothermic chemical reaction (thermal battery). The heat may be generated, for example, by reacting magnesium with water in the presence of iron. In one embodiment, water wicks into a chamber containing the magnesium-iron powder through a filter paper, which allows one to control the water flow rate and thus the reaction rate. The reactor's temperature is regulated and rendered independent of ambient temperatures with the aid of a phase change material (PCM). The utility of this integrated, self-heating cartridge is demonstrated by amplifying *E. Coli* DNA with the LAMP process and visually detecting the amplification products. The cartridge is particularly suitable for use in the field, in resource-poor regions of the world (where funds and trained personnel are in short supply), in remote areas, and at home. Other heat sources, such as battery-powered sources, solar-powered sources, and other heat sources that derive heat from exothermic reactions are all suitable.

The devices suitably include a heating material that undergoes an exothermic reaction upon contact with moisture. The devices also suitably include a thermal storage medium in thermal communication with the moisture-activated heating source. The thermal storage medium may be a phase-changing material. A conduit suitably places the heating material in fluid communication with a reservoir adapted to contain a fluid, with the conduit suitably wicking or otherwise transporting liquid from the reservoir to the moisture-activated heating source. It should be understood that the conduit may be tubular in configuration, but may also be an amount of a material (e.g., a strip) that conducts fluid to the moisture-activated heat source. It should also be understood that the term "moisture" does not refer only to water, as other fluids (e.g., alcohols, acids, bases, and the like) may serve to activate the heat sources.

The conduit suitably includes a fibrous material, a porous material, a channel patterned with pillars or similar features, or some combination of these. The conduit may also comprise a material that includes capillaries. Conduits that transport fluids by capillary action are considered especially suitable. A variety of materials can serve as conduits, including filter paper, cellulose, polytetafluoroethylene. (PTFE), nitrocellulose, an acrylic copolymer, polypropylene, polyethylene, polyvinylidene fluoride (PVDF), patterned channels, and the like. The conduit may include two different kinds of fibers, two materials having different porosity, or any combination thereof. Filter paper (and other materials that wick or transport material by way of capillary action) are considered especially suitable. Filter paper is readily available from many scientific supply houses. Other porous materials, including packaging materials, may also be used. The parameters (width, type of material, porosity) of the conduit material are easily adjusted so as to deliver the desired amount of fluid to the moisture-sensitive heating material.

The filter paper may—as shown in the attached figures—be configured as a pad or strip upon which the heating material sits. Filter paper may also be configured such that two or more strips of filter paper contact the heating material in two or more locations. The device may be constructed so as to include alternating layers of filter paper (or other fluid-transporting material) and heating material. The fluid conduit may also be a straw or other tube that is itself filled with fibers or a porous material or with packed beads or other materials to form a packed bed, so as to be capable of transporting fluid by way of capillary action. In some embodiments, the fluid may be transported to the moisture-sensitive heating material by way of a pump (motorized or manual), or even by gravity. In such an embodiment, the fluid may be positioned above the heating material and is delivered to the material by gravity flow, or even by a siphon.

The heating material (described in more detail below) is suitably in thermal communication with a reactor chamber, a fluidic element, or any combination thereof. The fluidic element may itself be thermally actuated. For example, the element may include a material that expands (reversibly or irreversibly) when heated. The element may include a material that shrinks (reversibly or irreversibly) when heated. In some embodiments, the heating material directly contacts the reactor chamber or fluidic element (e.g., conduit, valve, actuator, membrane, and the like). In other embodiments, a conductive material (e.g., metal) places the heating material in thermal communication with the reactor chamber or other element. The devices may also include one or more manually-operated elements that allows the user to place various components of the device into fluid or thermal contact with one another.

As discussed elsewhere herein, the moisture-sensitive heating material, once activated, serves to supply heat to the reactor chamber or other element. In this manner, a device can be constructed that is capable of performing a reaction or other process that requires heat, while requiring only the presence of moisture (e.g., water) to effect the heating. In some embodiments, an amount of fluid (e.g., water) is packaged with the device so that the fluid is available to the device at the time of activation. The fluid may be packaged in a baggie, a bladder, and the like. The user may release the fluid by opening a valve, puncturing the fluid's package, or otherwise placing the fluid in the package into fluid communication with the moisture-activated heat source.

The devices may include a reaction chamber that is an enzymatic amplification chamber. Such chambers may be adapted for isothermal amplification. The chamber may include one or more pre-stored (e.g., dried) reagents within. The chamber may also be an incubation chamber, or even a culture growth chamber.

A variety of fluidic elements may be present. Such elements may be valves, pistons, membranes, cantilevers, and the like. The element may be thermally-sensitive or thermally activated. For example, the valve may include a material that degrades (or expands) upon application of heat, such as Expancel™. Exemplary embodiments are described in U.S. application No. 61/446,850 (filed Feb. 25, 2011), in international application PCT/US2012/025196 (filed Feb. 15, 2012), and in Liu, Mauk, and Bau, "A disposable, integrated loop-mediated isothermal amplification cassette with thermally actuated valves," *Microfluidcs and Nanofluidics* (2011), the entireties of which are incorporated herein by reference. In this way, the moisture-activated heating material may be configured so as to supply sufficient heat to the element to open (or close) a valve.

Thermal storage media used in the disclosed devices may include a wax, a thermoplastic, a salt hydrate, a fatty acid, a fatty acid ester, or any combination thereof. Paraffin wax (detailed elsewhere herein) is considered a particularly suitable thermal storage medium. The thermal storage medium is suitably a material—such as wax—that undergoes a phase change at a particular temperature. As explained below, such materials permit the construction of devices that controllably maintain a particular temperature, which temperature is governed by the phase change (e.g., melting) temperature of the thermal storage material.

Various materials may be used as heating materials; materials that are moisture-reactive are considered especially suitable. Such materials include magnesium-iron alloy, calcium oxide, sodium acetate, potassium permanganate (reactive with glycerol), and the like.

Also provided are methods of processing a sample. These methods suitably include contacting a moisture-reactive heat source with a fluid (suitably delivered by capillary action) so as to generate heat; the moisture-reactive heat source being in thermal communication with a thermal (e.g., heat) storage medium. In one non-limiting embodiment, the moisture-reactive heat source and thermal storage medium may be configured to maintain the temperature of a sample in a reaction vessel adjacent to the water-sensitive heat source at a temperature in the range of from about 25 deg. C. to about 80 deg. C. for a period of time from about 0.5 to about 120 minutes in an environment of ambient temperature ranging from 5 deg. C. to 50 deg. C. It should be understood that the term "adjacent" does not require that the reaction vessel be in direct contact with the heat source. The methods also suitably include performing a nucleic acid amplification of the sample, e.g., PCR, loop-mediated amplification (LAMP), and the like. The methods may also include detecting the presence of one or more nucleic acids following amplification of the sample.

Exemplary Embodiments

The following embodiments are illustrative only, and do not serve to limit the scope of the present disclosure.

Figure 2:
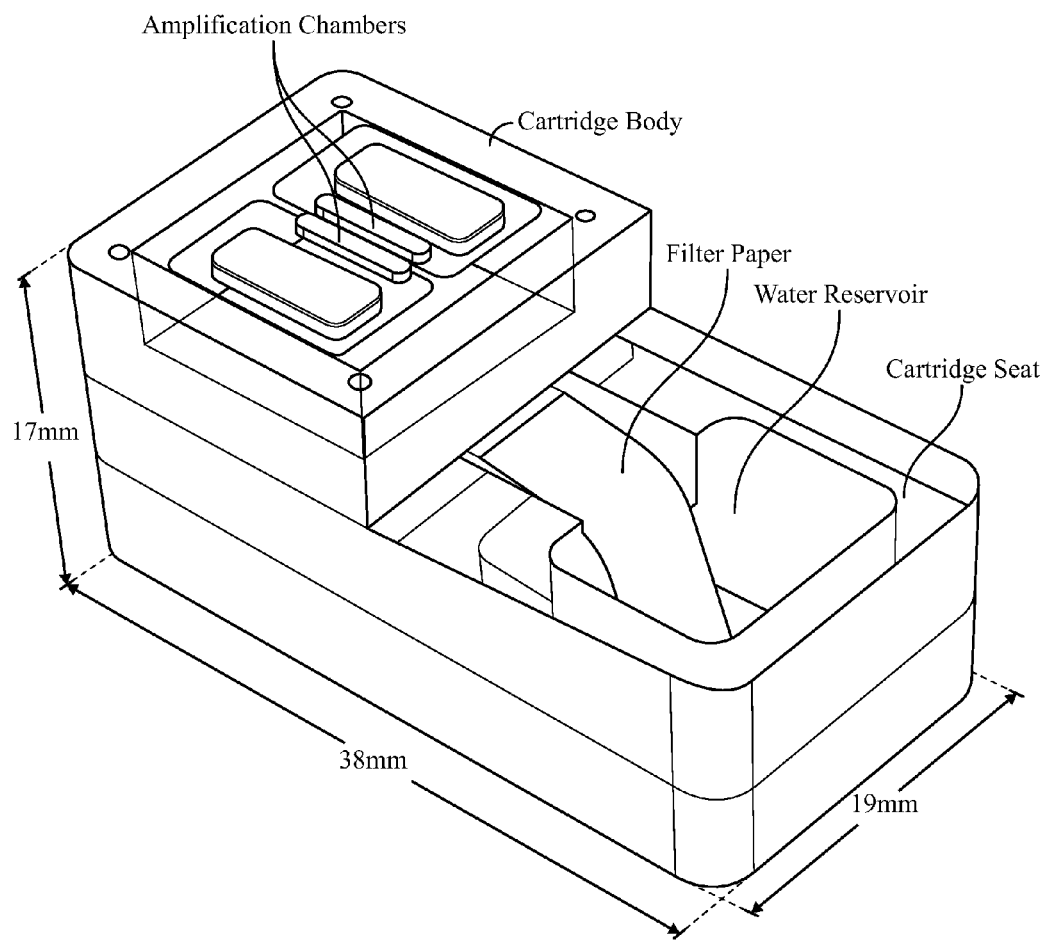
FIG. 2: A photograph of an exemplary water-activated, self-heating, non-instrumented cartridge for isothermal amplification of nucleic acids.

An exploded view of the water-activated, self-heating, non-instrumented cartridge for isothermal nucleic acid amplification is shown in FIG. 1. FIG. 2 features a photograph of the device. The 38 mm length×19 mm width×17 mm height, Polymethyl methacrylate (PMMA) cartridge consisted of two main components: a cartridge body and a cartridge seat. Both components were made with 5.5 mm (0.216 inch) thick, PMMA sheets. The cartridge and its components were milled with a precision, computer numerical control (CNC), milling machine (HAAS Automation Inc.). The various layers were solvent-bonded with acetonitrile (Sigma-Aldrich) at room temperature. Residual solvent was removed by overnight heating at 50° C.

The illustrative cartridge body contained two amplification chambers (additional chambers can be accommodated, when desired) and a self-regulated, exothermic reaction chamber. Each amplification chamber is 6.3 mm in length, 1.3 mm in width, 1.9 mm in depth, and 15.6 microliters in volume. The amplification chambers were located at the top of the self-heating chamber. The location of the amplification chambers allowed for easy optical access to the amplification chambers. The cartridge body was capped with a 1.5 mm (0.06 inch) thick, transparent Polymethyl methacrylate (PMMA) sheet. Inlet and outlet ports to the amplification chambers were vias formed in the cap film. The vias are connected to the amplification chambers through conduits milled in the upper surface of the cartridge body. The self-heating chamber (thermal battery) was 16 mm in length, 16 mm in width, and 3.2 mm in depth. The heating chamber contains, for example, Mg—Fe alloy (MRE Info. USA, see FIG. 7) surrounded with a casted, paraffin (Sigma-Aldrich) frame (see FIG. 8A). The melting temperature of the paraffin is 65° C., although phase change materials with other melting temperatures may be chosen.

The paraffin regulated the reaction chamber's temperature and, due to its low conductivity, also insulates the exothermic reaction chamber. To improve thermal isolation, both the amplification chambers and the self-heating chamber were surrounded with air-filled cavities. A piece of carbon black, double-sided, adhesive tape (Nisshin EM Corporation, Tokyo) was placed underneath the amplification chamber to reduce background fluorescence emission. The cartridge seat also housed a water reservoir and is capped at the bottom with a 250 mm (0.01 inch) thick, PMMA film. The water reservoir had a volume of 1.5 ml and is connected to the self-heating chamber with a filter paper.

Figure 8A:
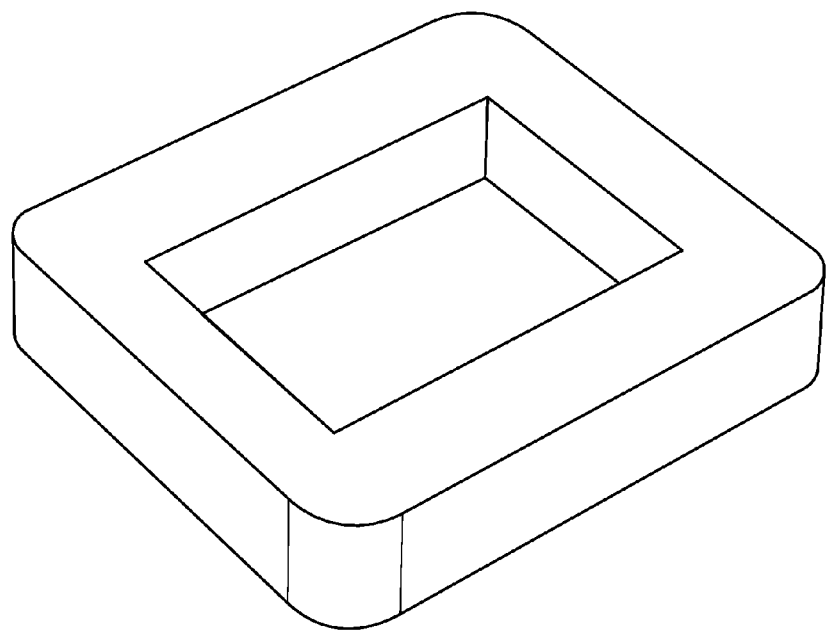
FIG. 8: A exemplary paraffin frame for thermal regulation of the exothermic reaction. (A) A photograph of the paraffin frame. (B) A schematic depiction of a paraffin frame fabrication process. (i) PDMS mold. (ii) PDMS mold filled with molten paraffin. (iii) The paraffin frame removed from the mold after cooling to room temperature.
Figure 8B:
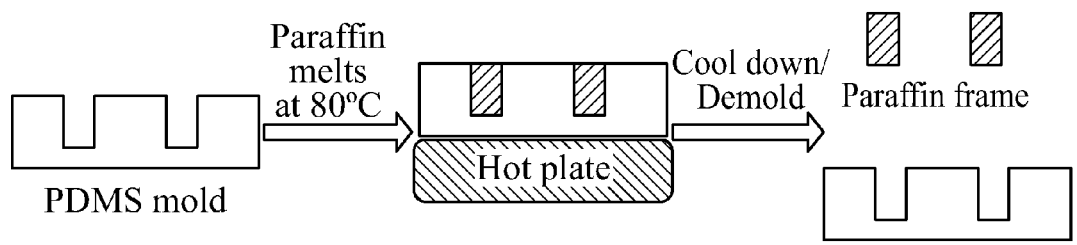

The 16 mm length×16 mm width×3.2 mm height paraffin frame was cast in a PDMS mold placed on a hot plate at 80° C. The fabrication of the paraffin frame is described in FIG. 8B. The frame was then inserted into the self-heating chamber and filled with 0.36 g of Mg—Fe alloy mixture. The paper strip was cut from a Whatman No. 1 filter paper (7 cm diameter, Whatman, Hillsboro, Oreg.) with a $CO_2$ laser machine (Universal Laser Systems). The filter paper strip provided a hydraulic connection between the water reservoir and the exothermic reaction chamber. A piece of 19 mm length×19 mm width, plastic food wrap (Polyvinyl Films, Inc., Sutton, Mass.) was positioned beneath the porous strip to prevent the powder from spilling out of the reaction chamber. Before heating, either the water reservoir was filled with water or the filter paper was brought into contact with pre-stored water in the water reservoir.

Temperature Measurement and Calibration

To evaluate the thermal performance of the reaction chambers, a calibration cartridge was constructed. The calibration cartridge was identical to the actual cartridge with the addition of a 1.0 mm diameter hole drilled in the top of the reaction chamber. A K-type thermocouple (Omega Engr., 75 μm in diameter wires, and a junction diameter of ~170 μm) was inserted in the reaction chamber through the drilled hole and sealed in place. The thermocouple wires were connected to a terminal block (SCC-68) that interfaced with a National Instruments data acquisition card (PXI-6281). Then, the reaction chamber was filled with DI water and its vias were sealed by using transparent tape (Scotch tape, 3M, St. Paul, Minn.) to prevent liquid evaporation during the heating process. Once the chemical, exothermic reaction was initiated by adding water into its water reservoir, the temperature was monitored and displayed using Labview™ software (National Instruments, Austin, Tex., USA).

Figure 9:
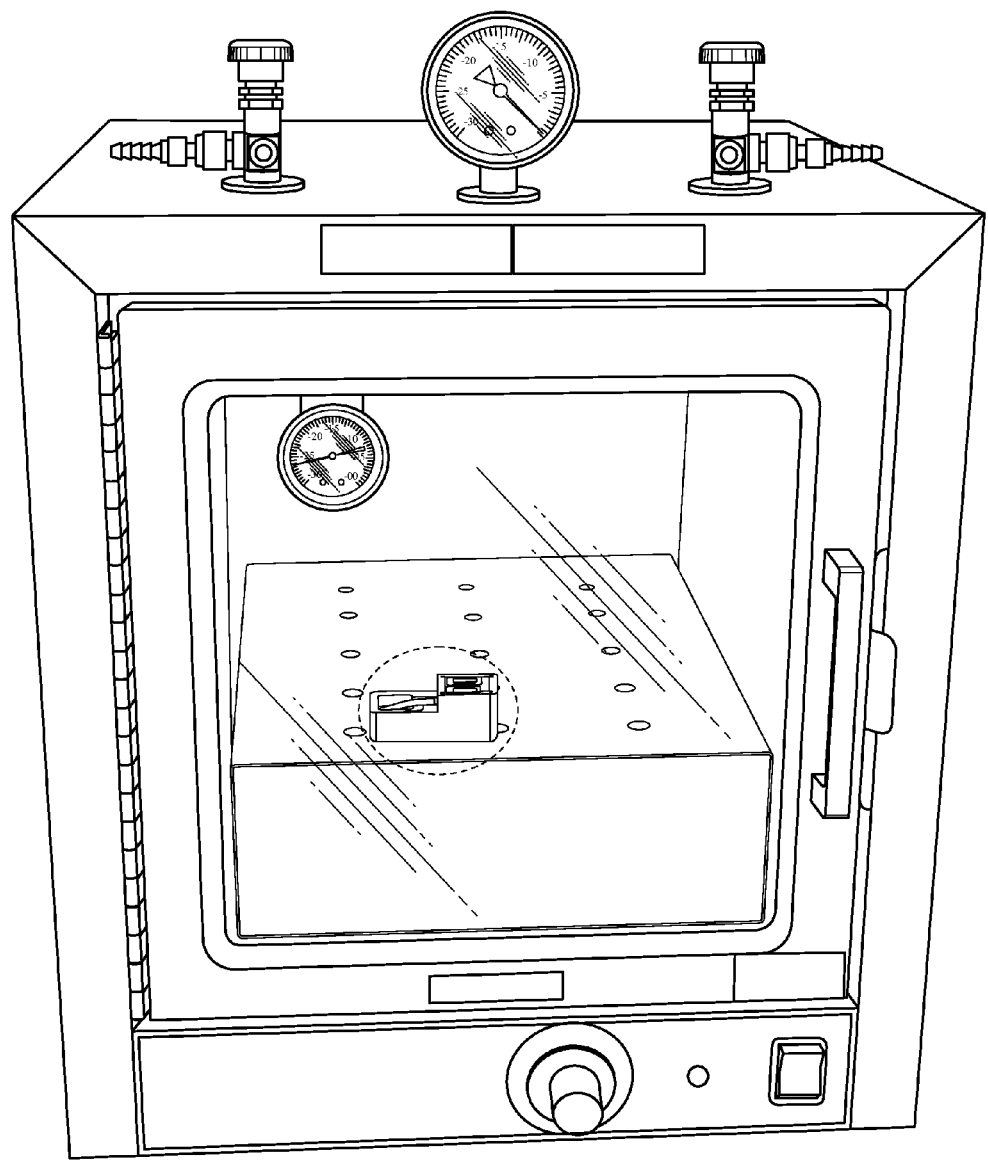
FIG. 9: To simulate various ambient temperatures, experiments were carried out in an oven (Isotemp Vacuum Oven Model 280A, Fisher Scientific Inc., Pittsburgh, Pa.).

To examine the effect of ambient temperature on the amplification chamber's temperature, experiments were carried out both at room temperature and at elevated temperatures (30° C. and 40° C.) in an oven (Isotemp Vacuum Oven Model 280A, Fisher Scientific Inc., Pittsburgh, Pa.). The setup for the calibration experiments is shown in FIG. 9.

E. Coli DNA LAMP Protocol

To demonstrate the applicability of the self-heating cartridge, the cartridge was used to amplify *E. coli* DNA. The LAMP template (plasmid DNA), extracted from pathogenic *E. coli* in urine samples and the primers for the *E. coli* amplification were a gift from Professor Abhay Vats (Department of Pediatrics, Children's Hospital of Pittsburgh, Pittsburgh, Pa.). The primers and their respective concentrations for *E. coli* DNA amplification were: outer primer F3 5'-GCCATCTCCTGATGACGC-3' (SEQ ID NO: 1) (0.2 microM), outer primer B3 5'-ATTTACCGCAGCCAGACG-3' (SEQ ID NO: 2) (0.2 microM), loop primer F loop 5'-CTTTGTAACAACCTGTCATCGACA-3' (SEQ ID NO: 3) (0.8 microM), loop primer B loop 5'-ATCAATCTCGATATCCATGAAGGTG-3' (SEQ ID NO: 4) (0.8 microM), inner primer BIP 5'-CTGGGGCGAGGTCGTGGTATTCCGACAAACACCACGAATT-3' (SEQ ID NO: 5) (1.6 microM), and inner primer FIP 5'-CATTTTGCAGCTGTACGCTCGCAGCCCATCATGAATGTTGCT-3' (SEQ ID NO: 6) (1.6 microM).43 The reaction mix also contained 20 mM Tris-HCl (pH 8.8), 10 mM KCl, 10 mM $(NH_2)_2SO_4$, 2 mM $MgSO_4$, 0.1% Triton X-100 (Sigma Chemical Co., MO), 0.8 M betaine (Sigma-Aldrich, St. Louis, Mo.), 8 units of Bst DNA polymerase (New England Biolabs, Inc., MA), 1.4 mM dNTPs, 15.0 μM SYTO® 9 Green (Molecular Probes, Inc., Eugene, Oreg.), and 5 μL of *E. coli* DNA at various concentrations. DNase/RNase-free water was used throughout the LAMP experiments.

Cartridge Operation and Visual Fluorescent Detection

First, 20 μl of LAMP master mix, which contains all the reagents necessary for LAMP, the fluorescent dye (SYTO® 9 Green), and the target molecules were injected into one of the amplification chambers through its inlet port. A similar mixture without the target DNA was injected into the second amplification chamber, which was used as a control. Next, the inlet and outlet ports were sealed using transparent tape to minimize evaporation and contamination during the amplification process. Then, 800 microliters of tap water was added to the water reservoir of the cartridge with a pipette. The water wicked through the filter paper strip into the exothermic reaction chamber to initiate and sustain the exothermic chemical reaction.

Figure 10:
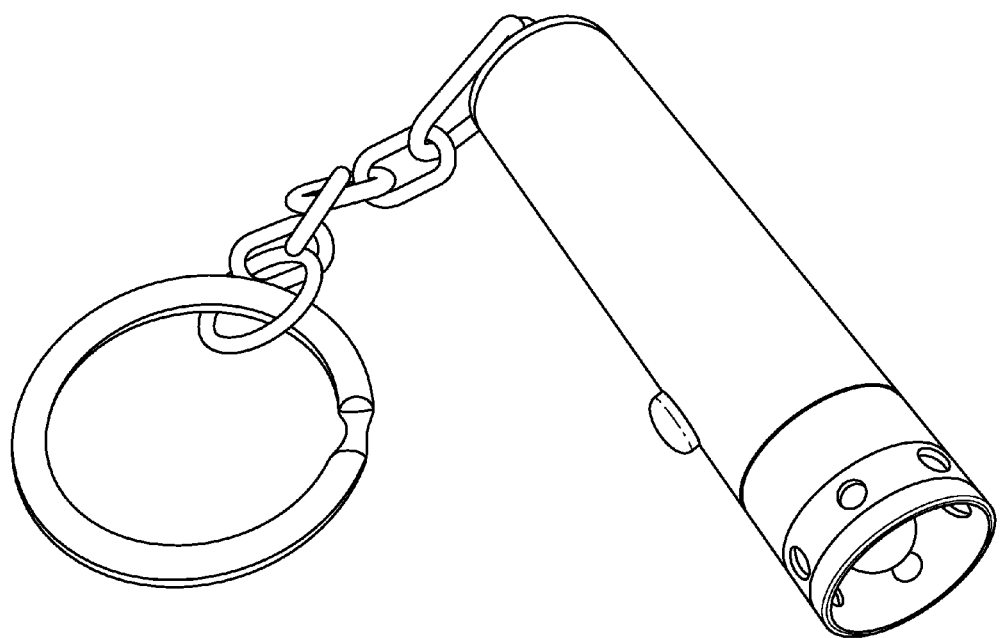
FIG. 10: A photograph of an exemplary keychain-size UV light source for fluorescent excitation (PickEgg Ltd, Hong Kong).

After about 1 hour, the cartridge was illuminated with a reusable, keychain-mounted UV light (UV money detector, PickEgg Ltd, Hong Kong, ~$2 unit price, shown in FIG. 10) in a darkened room. Green fluorescence emission from the two reaction chambers was directly observed by eye and/or recorded with a portable digital camera (Sony, DCR-PC330, Japan).

To confirm the end-point, visual fluorescence detection results, the LAMP reaction products were removed from the amplification chambers with a pipette and analyzed by gel electrophoresis. 5 μL of each LAMP-amplified product was loaded onto a lane of a 2.0% agarose gel. Electrophoresis of the amplified DNA fragment was carried out in TAE (Tris-Acetate-EDTA) buffer at a constant potential difference of 114 V for 40 minutes. DNA marker VIII (Roche Diagnostic, Indianapolis, Ind., USA) was concurrently used to gauge the sizes of the amplified DNA bands. The gel was stained with ethidium bromide and was visualized with UV illumination.

Additional Discussion

Flameless Exothermic Heater

Figure 7:
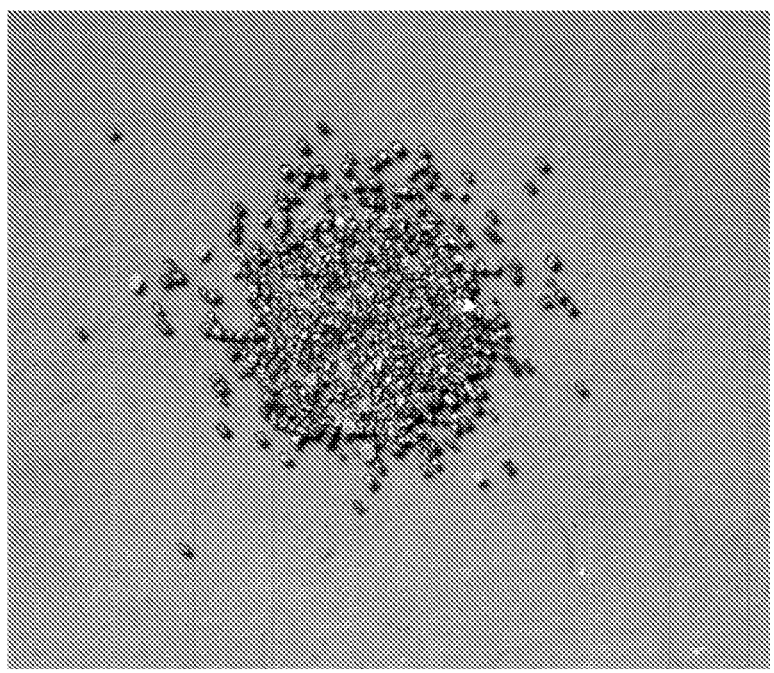
FIG. 7: A photograph of Mg—Fe alloy used in an exemplary exothermic reactor.

A commercially available, flameless ration heater (FRH) was selected as the self-heating material due to its ease of use, biodegradability, and safety. FRH is a water-activated, exothermic chemical compound that is included with Meals, Ready-to-Eat (MREs). This FRH consists of a powder mixture of Mg—Fe alloy, NaCl, antifoaming agents, and inert filler (FIG. 7).

In the presence of water, an exothermic, chemical reaction between the Mg—Fe alloy and the water occurs. The temperature can increase to well above 90° C. in several seconds. To control the rate of the reaction, one may control the rate of the water supply into the reaction chamber. One may use a porous, hydrophilic, filter paper strip to bridge the water reservoir and the exothermic reaction chamber. The filter paper was selected because of its good wetability, porous structure, and mechanical strength, although other materials may be used. Once water is added into the water reservoir, it is absorbed by the filter paper and wicks into the exothermic reaction chamber by capillary action without a need for any external pumps. The rate of water flow depends on the width and thickness of the strip.

Figure 3:
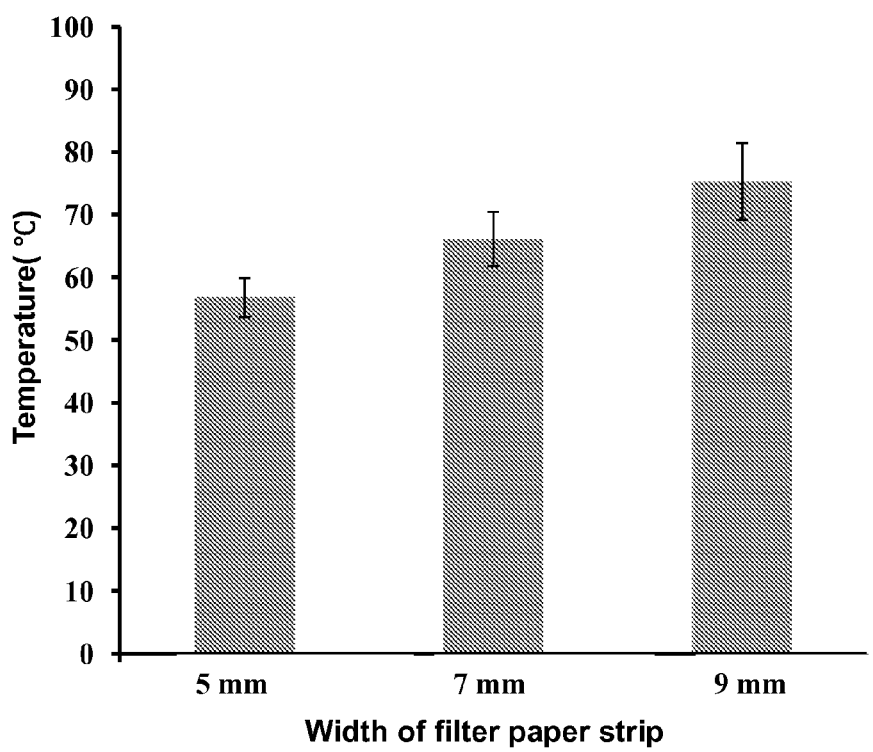
FIG. 3: An exemplary amplification chamber's temperature as a function of the filter paper strip's width (n=3). The room temperature is ~22° C. (without phase change material).

To evaluate the effect of the filter paper strip's size on the amplification chamber's temperature, three filter paper strips with different widths (5.0 mm, 7.0 mm and 9.0 mm) were tested at room temperature (~22° C.) and in the absence of the paraffin frame. FIG. 3 depicts the exothermic reaction chamber's temperature as a function of the strips' width. The wider the filter paper strip was, the higher was the amplification chamber's temperature. This experiment illustrates that the amplification chamber's temperature can be controlled by adjusting the width of the filter paper strip. In all the experiments described later in the paper, a 7.0 mm wide filter paper strip was used as it enabled amplification chamber temperatures between 60-65° C., which is the desired temperature range for the LAMP reaction.

Temperature-Regulation with Phase Change Material

In the previous section, it was demonstrated that when the ambient temperature is fixed, the amplification chamber's temperature can be controlled by adjusting the rate of the water supply. For the device to be useful in the absence of climate control and to be independent of varying ambient conditions, it is necessary to isolate the amplification chamber's temperature from ambient conditions. One may accomplish this objective with the use of the phase change material. To demonstrate the regulating effect of the phase change material, the amplification chamber's temperature was monitored in the absence and the presence of the phase change material at three different ambient temperatures: 22° C., 30° C., and 40° C. The elevated ambient temperatures were maintained by carrying out the experiment in an oven (FIG. 9).

Figure 4:
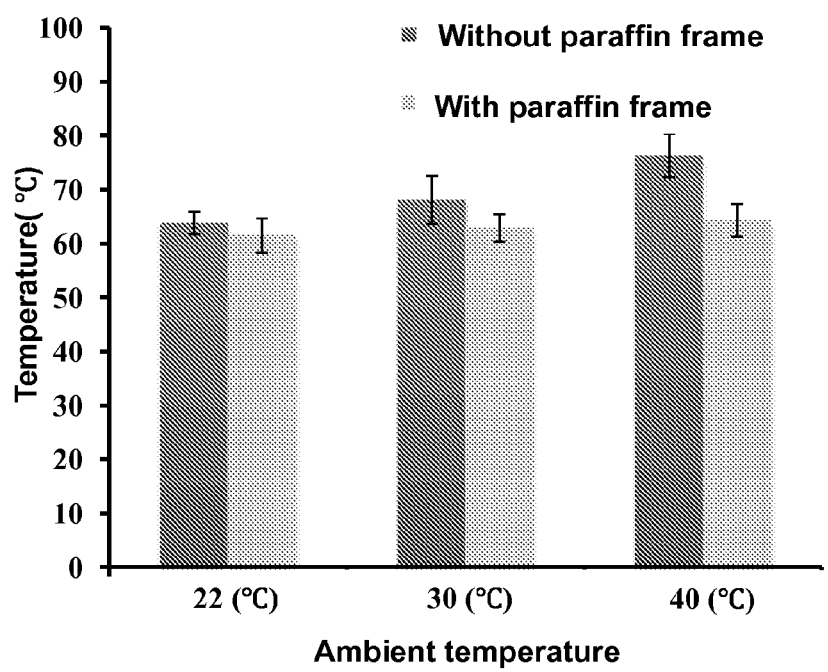
FIG. 4: An exemplary amplification chamber's temperature as a function of the ambient temperature in the absence (darker bars) and the presence (lighter bars) of a regulating phase change material (n=3).

FIG. 4 depicts the average reaction chamber temperature in the absence (left-hand bar at each temperature) and the presence (right-hand bar at each temperature) of the phase change material as a function of the ambient temperature. The reported temperature is the amplification chamber's average temperature during an one hour period (once the chamber's temperature was increased from ambient value to the amplification temperature). The error bars correspond to the scatter of the temperature in three devices. In the absence of the moderating effect of the phase change material, the amplification chamber's temperature increased from 63° C. at ambient temperature of 22° C. to 75° C. at the ambient temperature of 40° C. Although the LAMP process is robust when faced with temperature variations, temperatures above 70° C. may in some cases affect enzyme activity. In contrast, in the presence of the phase change material, the amplification chamber's temperature was nearly independent of the ambient temperature and was retained at 64.1±3° C., even when the ambient temperature was 40° C. The figure demonstrates that the paraffin can successfully regulate the temperature by absorbing excess heat as latent heat during melting and, if necessary, releasing the stored heat during solidification.

Figure 5:
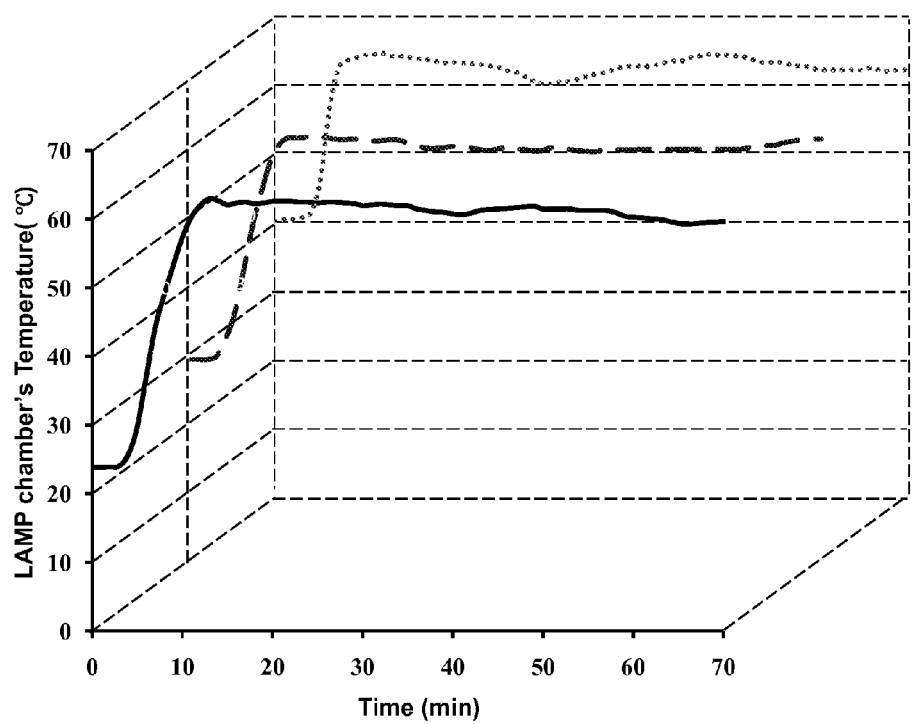
FIG. 5: An exemplary amplification chamber's temperature as a function of time when the ambient temperature is 22° C. (solid line), 30° C. (dashed line), and 40° C. (dotted line).

FIG. 5 depicts the amplification chamber's temperature as a function of time when the ambient temperature is 22° C. (solid line), 30° C. (dashed line), and 40° C. (dotted line). Time zero is set to coincide with the instant when water is added into the water reservoir. Once water has been introduced into the cartridge, it takes nearly 10 minutes for the water to migrate into the exothermic reaction chamber and to raise the cartridge's temperature to ~60° C. This experiment used 0.36 g of Mg—Fe alloy mixture and 0.8 ml of water. The amount of the reactants used in the experiments is about 50 fold smaller than previously reported in a self-heating experiment. When the ambient temperature is 22° C., the amplification chamber's temperature ranged from 59.3 to 62.5° C. for about an hour, which is longer than typically necessary to amplify the target molecules to detectable levels. Since the LAMP reaction operates effectively over a relatively broad temperature range (i.e., 60-65° C.), the temperature range maintained in the experiments is quite adequate. With optimization and use of multiple exothermic reaction chambers, the time needed to ramp up the temperature can be shortened.

E. coli DNA Amplification and Visual Detection

To demonstrate that the device can be used to carry out the amplification process, a target DNA was amplified from the bacterium E. coli. E. coli is the second major cause of neonatal meningitis, which is a significant cause of mortality among newborns. It is also associated with a high incidence of neurological sequelae.

Because the LAMP process is highly efficient, it is capable of amplifying low abundance targets to detectable quantities within less than an hour. LAMP products can be directly detected by visual observation of end-point turbidity or fluorescence with the naked eye. Here, one may use the fluorescent emission of the intercalating dye Syto Green to directly observe the LAMP products. To reduce interference from background fluorescence emitted by the PMMA cartridge itself and the Mg—Fe alloy, a piece of carbon black, double-sided adhesive tape was inserted underneath the amplification chambers. Separate experiments (not reported here) determined that the carbon black tape emits negligible background fluorescence.

Figure 6A:
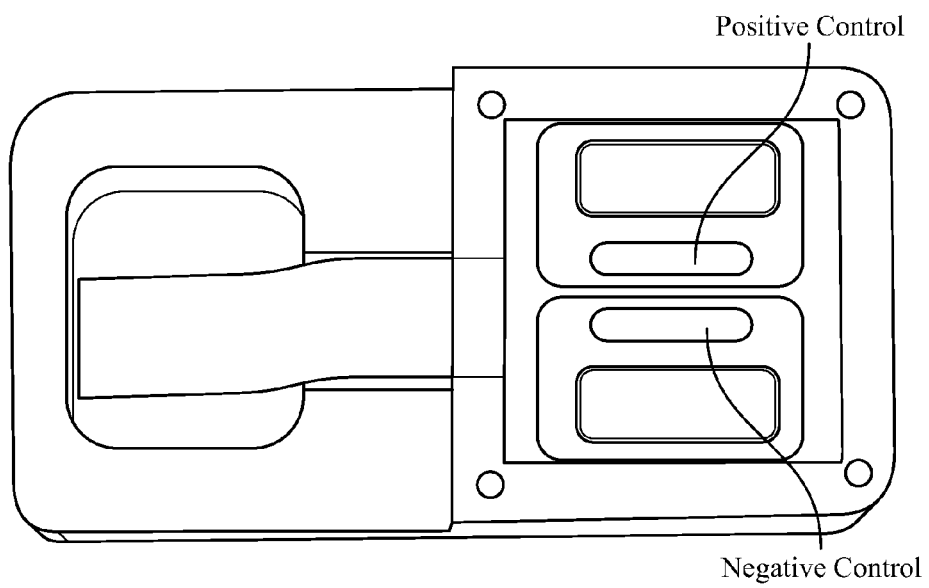
FIG. 6: (A) Green fluorescent emission from a test amplification chamber in ten target $E.$ $coli$ DNA molecules which were amplified and from a negative control reaction chamber. The emission source is a mini keychain UV light. (B) Electropherograms of LAMP products (5.0 µL) of $E.$ $coli$ DNA in a 2% agarose gel. Lane M, DNA marker VIII. Lanes 1, 2, and 3 correspond, respectively, to 100, 10, and 0 (negative control) target copies per reaction chamber.

FIG. 6A shows the fluorescence images of the E. coli positive sample (10 target copies) and negative sample (0 target molecules, no template) in the self-heating LAMP cartridge after LAMP amplification at room temperature (~22° C.) for 60 minutes. The reaction chambers were excited with a low cost (~$2.00), reusable UV source (which is commonly used to detect forged bills). There is a difference between the signal intensity emitted by the test chamber compared with that emitted by the negative control chamber. Emission from the paraffin frame can be reduced by encircling the reaction chambers with black tape.

The use of in-situ fluorescent detection simplifies cartridge design and operation as it eliminates the need to transfer the reaction products from the amplification chamber to the detection chamber. The in-situ fluorescent detection also reduces analysis time. The amplification chamber can be illuminated at various stages of the process and the test can be concluded as soon as a detectable signal is observed. The devices described herein do not require any instrumentation to operate.

Variants of the device can include continuous detection of the fluorescent emission with a CCD camera instead of the end-point detection described herein. The use of a camera would allow measurement of emitted signal intensity as a function of time and quantification. Yet another variant of the device can include discharge of the amplification products (when appropriately functionalized primers are used) onto a lateral flow strip. The lateral flow strip can offer the ability of detecting multiple targets.

Figure 6B:
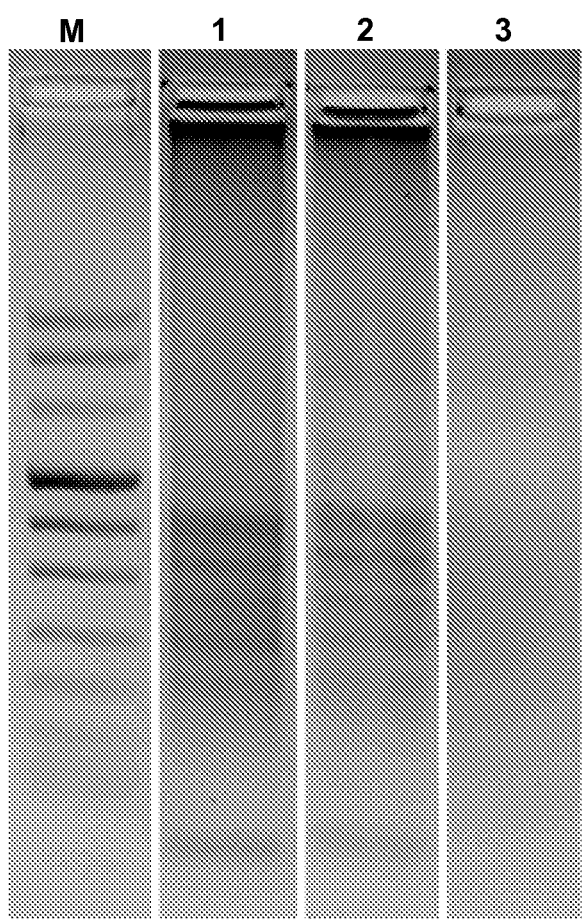

To verify the visual detection results, one may subject LAMP products to gel electrophoresis. FIG. 6B shows a sample of electropherograms of ethidium bromide, stained LAMP products in 2% agarose gel. Lane M is the DNA marker VIII. Lanes 1, 2, and 3 correspond, respectively, to LAMP cartridge products with 100, 10, and 0 (negative control) copies. The results clearly indicate that as few as 10 E. coli DNA copies can be comfortably detected on the cartridge. Each experiment was repeated three times with similar results. This is a comparable performance to that of state of the art benchtop thermocyclers as well as with the integrated cartridge which was heated with a thin film heater.

Further utility was demonstrated by amplifying and detecting Escherichia coli DNA with loop mediated isothermal amplification (LAMP). The device can detect consistently as few as 10 target molecules in the sample. With proper modifications, the cartridge also can work with other isothermal nucleic acid amplification technologies for detecting nucleic acids associated with various pathogens borne in blood, saliva, urine, and other body fluids as well as in water and food. The disclosed devices are suitable for use at home, in the field, and in limited-resource settings, where access to sophisticated laboratories is impractical.

Further Discussion

Presented is a low-cost, disposable, water-activated, self-heating, non-instrumented, microfluidic cartridge for nucleic acid amplification and detection. The device utilizes the exothermic reaction between Mg—Fe alloy and water as the heat source. The reaction rate is controlled by using a filter paper to control the water flow rate from a water reservoir to the exothermic reaction chamber. The amplification chambers' temperatures are regulated with a phase change material (i.e., paraffin) and maintained at a desired level, suitable for LAMP-based amplification, independent of the ambient temperature, over a wide range of ambient temperatures ranging from 20° C. to 40° C.

To demonstrate the device's utility for nucleic acid amplification, E. coli DNA were amplified and detected and were detectable down to 10 target molecules in the sample. The performance of the device is comparable to that of the state of the art, benchtop PCR machines and with the integrated cartridge heated with a thin film heater. Amplification results were obtained by exciting a fluorescent signal with a mini, reusable, inexpensive (less than about $2) keychain UV light and observed the emitted signal by eye without any instrumentation. The visual test can provide qualitative results; monitoring the emission with a CCD camera, such as is available in cell phones, or photodiodes, one can measure signal intensity as a function of time and quantify the number of target molecules in the sample.

If desired, the devices can be interfaced with a lateral flow strip and the amplification products can be detected with labels such as gold particles. Lateral flow strip based detection would require, however, the discharge of the products onto a lateral flow strip, which would require additional flow control. The lateral flow strip may have, however, the advantage of allowing for the concurrent identification of multiple targets when a multiplexed LAMP reactor is used.

The self-heated cartridge system is useful in rapid, inexpensive diagnosis of infectious diseases at the point of care. LAMP is, of course, just one example of an isothermal amplification process, and other processes may be used. With proper modification, the cartridge also can work with other isothermal nucleic acids amplification techniques.

Future modifications and improvements of the cartridge will include dry storage of LAMP/RT-LAMP reagents in the amplification chamber. This can be achieved by encapsulating the dry reagents with paraffin, which will melt upon heating of the reaction chamber to the desired incubation temperature, move out of the way, and allow the hydration of the reagents. Another improvement may include equipping the cartridge with a solid phase membrane for the isolation, concentration, and purification of nucleic acid targets.

The fully integrated, non-instrumented cartridge can be operated at the point of care by minimally trained personnel and can carry out all the necessary steps from sample to answer. With appropriate modifications of the reagents, the system can be used to detect various infectious diseases, monitor the health of individuals, provide a trigger for the administration of expensive or dangerous medications, and facilitate monitoring water and food quality. The device is suitable for use in the field, in resource-poor regions, in remote areas, and at home. Additional information may be found in Liu et al., Lab Chip, 2011, 11, 2686-2692.

What is claimed:

1. A device, comprising:
a heating material that undergoes an exothermic reaction upon contact with moisture;
a thermal storage medium in thermal communication with the moisture-activated heating source, the thermal storage medium comprising a phase-changing material; and
a conduit placing the heating material in fluid communication with a reservoir adapted to contain a fluid, the conduit comprising a material capable of transporting liquid by capillary action,
wherein the heating material is in thermal communication with an enzymatic amplification reaction chamber, a thermally-actuated fluidic element, or any combination thereof.

2. The device of claim 1, wherein the conduit comprises a fibrous material.

3. The device of claim 2, wherein the fibrous material comprises filter paper, cellulose, polytetafluoroethylene (PTFE), nitrocellulose, an acrylic copolymer, polypropylene, polyethylene, polyvinylidene fluoride (PVDF), or any combination thereof.

4. The device of claim 1, wherein the conduit comprises a material comprising two or more different fiber sizes, two or more different pore sizes, or both.

5. The device of claim 1, wherein the enzymatic amplification chamber is adapted for isothermal amplification.

6. A device, comprising:
a heating material that undergoes an exothermic reaction upon contact with moisture;
a thermal storage medium in thermal communication with the moisture-activated heating source, the thermal storage medium comprising a phase-changing material; and
a conduit placing the heating material in fluid communication with a reservoir adapted to contain a fluid, the conduit comprising a material capable of transporting liquid by capillary action,
wherein the heating material is in thermal communication with an incubation and culture growth reaction chamber, a thermally-actuated fluidic element, or any combination thereof.

7. The device of claim 1, wherein the thermally-actuated fluidic element comprises a valve, a piston, a membrane, a cantilever, thermally-releasable reagents, or any combination thereof.

8. The device of claim 1, wherein the thermal storage medium comprises a wax, a thermoplastic, a salt hydrate, a fatty acid, a fatty acid ester, or any combination thereof.

9. The device of claim 1, wherein the heating material comprises magnesium-iron alloy, calcium oxide, sodium acetate, potassium permanganate, or any combination thereof.

10. The device of claim 6, wherein the thermally-actuated fluidic element comprises a valve, a piston, a membrane, a cantilever, thermally-releasable reagents, or any combination thereof.

* * * * *

SEQUENCE LISTING

<160> NUMBER OF SEQ ID NOS: 6

<210> SEQ ID NO 1
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1
gccatctcct gatgacgc                                                    18

<210> SEQ ID NO 2
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 2
atttaccgca gccagacg                                                    18

<210> SEQ ID NO 3
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 3
ctttgtaaca acctgtcatc gaca                                             24

<210> SEQ ID NO 4
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 4
atcaatctcg atatccatga aggtg                                            25

<210> SEQ ID NO 5
<211> LENGTH: 40
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 5

```
ctggggcgag gtcgtggtat tccgacaaac accacgaatt                              40

<210> SEQ ID NO 6
<211> LENGTH: 42
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 6
cattttgcag ctgtacgctc gcagcccatc atgaatgttg ct                           42
```